United States Patent [19]
Lüchinger

[11] Patent Number: 5,948,884
[45] Date of Patent: Sep. 7, 1999

[54] CYCLOSPORIN DERIVATIVES WITH ANTI-HIV EFFECT

[75] Inventor: Jean Martin Lüchinger, Basel, Switzerland

[73] Assignee: C-Chem AG, Switzerland

[21] Appl. No.: 08/981,597

[22] PCT Filed: Jul. 17, 1996

[86] PCT No.: PCT/EP96/03129

§ 371 Date: Dec. 31, 1997

§ 102(e) Date: Dec. 31, 1997

[87] PCT Pub. No.: WO97/04005

PCT Pub. Date: Feb. 6, 1997

[30]     Foreign Application Priority Data

Jul. 17, 1995 [EP] European Pat. Off. ............... 95111162

[51] Int. Cl.⁶ ...................................................... C07K 7/00
[52] U.S. Cl. .............................. 530/317; 530/327; 514/9; 514/11
[58] Field of Search .................................... 530/317, 327; 514/9, 11

[56]                References Cited

PUBLICATIONS

Billich et al, Journal of Virology, vol. 69, No. 4, pp. 2451–2461, 1995.
Karpas, etal, Proc. Natl. Acad. Sci USA 89(1992) pp. 8351–8355.

*Primary Examiner*—Cecilia J. Tsang
*Assistant Examiner*—C. Delacroix-Muirheid
*Attorney, Agent, or Firm*—Wenderoth, Lind & Ponack, L.L.P.

[57]                ABSTRACT

The invention concerns new cyclic peptides of general formula (I)

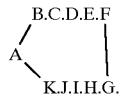

in which the letters A to K signify residues of the following amino acids: A is substituted homothreonine of the general formula (II):

$$R_1-CH_2CH(CH_3)-CH(OH)-CH(NHCH_3)-COOH$$

in which $R_1$ is n-propyl or propenyl in which the double bond is preferably in the trans configuration; B is α-aminobutyric acid, valine, norvaline or threonine; C is a D-amino acid of the general formula (III):

$$CH_3NH-CH(R)-COOH$$

in which R is straight-chain or branched-chain $C_2$–$C_6$ alkyl, alkenyl or alkynyl, whereby these groups may be substituted by hydroxy, amino, $C_1$–$C_4$ alkylamino, $C_1$–$C_4$ dialkylamino, alkoxy or acyloxy, $COOR_2$ or $CONHR_2$ in which $R_2$ is straight-chain or branched-chain $C_1$–$C_4$ alkyl X—$R_3$ in which X is O or S and $R_3$ is straight-chain or branched-chain $C_1$–$C_4$ alkyl, alkenyl or alkynyl and, when X is S, $R_3$ may also by aryl or heteroaryl, halogen, preferably fluorine, cyano, $CHR_4R_5$ in which $R_4$ is hydrogen, methyl, ethyl or phenyl and $R_5$ is hydrogen, hydroxy, halogen (preferably fluorine), amino, $C_1$–$C_4$ alkylamino, $C_1$–$C_4$ dialkylamino, acyloxy (preferably acetyloxy), tert-butoxycarbonylamino-ethoxy-ethoxy-acetyloxy or alkoxycarbonyl (preferably butoxycarbonyl); D is N-methyl-gamma-hydroxyleucine or N-methyl-gamma-acetyloxyleucine; E is valine; F, I and J are each N-methylleucine; G is alanine; H is D-alanine or D-serine; and K is N-methylvaline. The invention also concerns the preparation of such peptides and their use in the prevention of infection by the human immunodeficiency virus (HIV).

15 Claims, No Drawings

CYCLOSPORIN DERIVATIVES WITH ANTI-HIV EFFECT

This is a 371 of PCT/EP96/03129, filed Jul. 17, 1996.

BACKGROUND AND PRIOR ART

The present invention relates to novel cyclic peptides from the cyclosporin series which have a strong inhibitory effect on human immunodeficiency virus (HIV) without having any immunosuppressive activity. Such cyclic peptides are claimed, inter alia, in EP 484 281. One of the substances which is specifically claimed in this patent specification is (gamma-hydroxy-N-methylleucine)cyclosporin. While this substance can very readily be prepared from cyclosporin A by means of microbial hydroxylation, EP 484 281 indicates that this substance has an activity against HIV which is some 5–6 times weaker than that of the most strongly active substances, namely MeIle-4-cyclosporin or MeVal-4-cyclosporin. All 3 substances have practically no immunosuppressive activity. Unexpectedly, it has been found that the anti-HIV effect of (gamma-hydroxy-MeLeu-4)cyclosporin can be substantially improved, without giving rise to any immunosuppressive activities, by introducing suitable substituents into the methylene group of the amino acid sarcosine in position 3 of said cyclosporin. Since the therapeutic doses of cyclosporin A which are used after organ transplants in order to prevent rejection of the transplanted organs are very high, and similarly high doses are to be expected for an anti-HIV therapy which uses cyclosporin derivatives, the value of the present invention is that it provides novel cyclosporin derivatives which possess high anti-HIV activity and that these cyclosporin derivatives can be prepared simultaneously, in a few steps, from cyclosporin A, which is a product which is already being prepared by the ton.

BRIEF SUMMARY OF THE INVENTION

The present invention consequently relates to novel cyclic peptides of the general formula

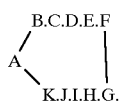

I in which A to K denote residues of the following amino acids:

A is a substituted homothreonine of the general formula $$R_1-CH_2CH(CH_3)-CH(OH)-CH(NHCH_3)-COOH \quad II$$

in which $R_1$ is n-propyl or propenyl and the double bond is preferably trans-configured, B is alpha-aminobutyric acid, valine, norvaline or threonine, C is a (D)-amino acid of the general formula $$CH_3NH-CH(R)-COOH \quad III$$

in which
R is
$C_2-C_6$ alkyl, alkenyl, alkynyl, straight-chain or branched, where these groups can additionally be substituted by hydroxyl, amino, $C_1-C_4$ alkylamino, $C_1-C_4$ dialkylamino, alkoxy or acyloxy, $COOR_2$, $CONHR_2$, where $R_2$ can be $C_1-C_4$ alkyl, straight-chain or branched, $X-R_3$, where X is O or S, and $R_3$ is $C_1-C_4$ alkyl, alkenyl or alkynyl, straight-chain or branched, and where, when X is S, $R_3$ can also be aryl or heteroaryl, halogen, preferably fluorine, cyano, or $CHR_4R_5$, where $R_4$ is hydrogen, methyl, ethyl or phenyl, and $R_5$ is hydrogen, hydroxyl or halogen, preferably fluorine, and, furthermore, amino, $C_1-C_4$ alkylamino, $C_1-C_4$ dialkylamino, acyloxy, preferably acetyloxy, and, furthermore, tert-butoxycarbonyl-aminoethoxy-ethoxy-acetyloxy, or alkoxycarbonyl, preferably butoxycarbonyl, D is N-methyl-gamma-hydroxyleucine or N-methyl-gamma-acetyloxyleucine, E is valine, F, I and J are in each case N-methylleucine, G is alanine, H is (D)-alanine or (D)-serine, and K is N-methylvaline.

DETAILED DESCRIPTION

An important element in the present invention is the variation of the radical R in formula III of the amino acid C.

Examples of the radical R in formula III are $C_1-C_6$ alkyl, alkenyl or alkynyl, straight-chain or branched, where these groups can additionally be substituted by hydroxyl, alkyloxy, acyloxy, $C_1-C_4$ alkylamino or $C_1-C_4$ dialkylamino. Examples are methyl, ethyl, propyl, isopropyl, n-butyl, isobutyl, tert-butyl, pentyl, isopentyl, neopentyl, tert-pentyl, hexyl, cyclopropylmethyl, allyl, butenyl, pentenyl, isopentenyl, propargyl and butynyl. Examples of the alkyloxy and acyloxy substituents in the radical R are methoxy, ethoxy, propyloxy, beta-methoxyethoxy, and also acetoxy or pivaloyloxy. Examples of the $C_1-C_4$ alkylamino and $C_1-C_4$ dialkylamino substituents in the radical R are methylamino, dimethylamino, ethylamino, diethylamino, propylamino, isopropylamino, dipropylamino, diisopropylamino and tert-butylamino. The radical $R_2$ in R can have the meaning of methyl, ethyl, propyl, isopropyl, n-butyl, isobutyl or tert-butyl. Furthermore, R can also have the meaning of halogen or cyano. The radical $R_3$ in $X-R_3$ can be straight-chain or branched $C_1-C_4$ alkyl, alkenyl or alkynyl, and, when X is S, can also be aryl or heteroaryl. Examples of aryl are phenyl, 1-naphthyl and 2-naphthyl, and examples of heteroaryl are 2-pyridyl, 3-pyridyl, 4-pyridyl, 2-pyrimidinyl, 4-pyrimidinyl, pyrazinyl and benzothiazol-2-yl.

Preferred compounds are those in which the radical $R_1$ in A is propenyl, B is alpha-aminobutyric acid, D is N-methyl-gamma-hydroxyleucine, E is valine, F, I and J are in each case N-methylleucine, G is alanine, H is (D)-alanine and K is N-methylvaline.

In this configuration, the radical R in the formula III is methyl, ethyl, propyl, allyl, propargyl, hydroxymethyl, hydroxyethyl, hydroxybenzyl, aminomethyl, methylaminomethyl, dimethylaminomethyl, ethylaminomethyl, diethylaminomethyl, propylaminomethyl, isopropylaminomethyl, dipropylaminomethyl, diisopropylaminomethyl, tert-butylaminomethyl, fluoromethyl, methoxymethyl, ethoxymethyl, methoxycarbonyl, ethoxycarbonyl, propoxycarbonyl, isobutyloxycarbonyl, methylaminocarbonyl, ethylaminocarbonyl, propylaminocarbonyl, isopropylaminocarbonyl, phenylaminocarbonyl, methoxycarbonylmethyl, ethoxycarbonylmethyl, propoxycarbonylmethyl, tert-butoxycarbonylmethyl, methoxy, ethoxy, propoxy, isopropoxy, n-butoxy, isobutoxy, tert-butoxy, hydroxyethoxy, methylthio, ethylthio, hydroxyethylthio, propylthio, isopropylthio, n-butylthio, isobutylthio, tert-butylthio, phenylthio, 2-pyridylthio, benzothiazol-2-ylthio, cyano or fluorine.

The novel compounds can be prepared by using suitable bases to prepare a polyanion from cyclic peptides of the general formula I, in which D has the meaning of N-methylleucine, reacting this polyanion with suitable electrophiles and, where appropriate, subjecting the newly introduced radical to further transformation in order to obtain the desired substitution of the amino acid C. The resulting products are then hydroxylated by means of microbial transformation. Another option for preparing the novel compounds consists, as described above, in using suitable bases to prepare a polyanion from cyclic peptides of the general formula I, in which the amino acid D has the meaning of N-methyl-gamma-hydroxy-leucine, reacting this polyanion with suitable electrophiles and, where appropriate, subjecting the newly introduced radical to further transformation in order to obtain the desired substitution of the amino acid C. The polyanions are prepared by reacting a solution of the starting compound in a suitable anhydrous solvent, such as tetrahydrofuran, at low temperatures, preferably at temperatures of below minus forty degrees, with an excess of a suitable base, preferably lithium diisopropylamide, dissolved in anhydrous tetrahydrofuran, and capturing the resulting polyanion with a suitable electrophile. This method essentially corresponds to that described by Seebach (D. Seebach et al., Helv. Chim. Acta, Vol. 76, 1564–1590, 1993). Further bases which are suitable are other alkali metal amides, such as lithium diethyl-amide or lithium hexamethyldisilazide, and also alkali metal alcoholates, such as potassium methoxide, potassium tert-butoxide, potassium tert-amoxide and sodium methoxide. Examples of suitable electrophiles are alkyl halides, such as methyl iodide, ethyl iodide, allyl bromide and benzyl bromide, alkoxymethyl halides, such as methoxymethyl chloride, methoxyethoxymethyl chloride and benzyloxymethyl chloride, or else carbonyl compounds, such as aldehydes or some ketones, for example formaldehyde, acetaldehyde, benzaldehyde, acetone or cyclic ketones such as cyclopropanone and its higher homologs, and also reactive derivatives of carbonic acid, such as isocyanates, and of organic carboxylic acids, such as esters, e.g. ethyl formate, diethyl oxalate, ethyl benzoates and ethyl nicotinates. Other suitable electrophiles are halogens and also other sources of positive halogen such as N-chlorosuccinimide, N-bromosuccinimide, N-fluoro-N-neopentyl-p-toluenesulfonamide, perchloryl fluoride, N-halocyanogens, such as cyanogen chloride, and also disulfides and their sulfonium salts, such as dimethyl sulfide, dimethylthiomethylsulfonium iodide, diphenyl disulfide, dipyridyl disulfide and 2,2'-benzothiazolyl disulfide. The reactions of these electrophiles lead to the formation of a new center of chirality. Mixtures in which one of the two possible diastereomers predominates are obtained in dependence on the reaction conditions. These newly formed diastereomers differ from each other in that the amino acid C in the general formula I has the (D) configuration in one case and the (L) configuration in the other case. In the present invention, those diastereomers in which the amino acid C in the general formula I is given the (D) configuration are preferred. The factors which lead to the preferred formation of the (D) diastereomer or the (L) diastereomer, and also the influence of the bases employed, and a broad range of electrophiles, were investigated in detail by Seebach for the case where cyclosporin A is the starting compound, are described in the literature (D. Seebach et al., Helv. Chim. Acta, Vol. 76, 1564–1590, 1993), and have been commented on critically by other authors (S. David, Chemtracts Organic Chemistry, Vol. 6, 303–306, 1993). The experimental conditions which are described in the present invention lead predominantly to the formation of those diastereomers in which the newly formed center of chirality of the amino acid C has the (D) configuration. It was demonstrated in the present invention that this is also the case when 4-(gamma-hydroxy)-N-methyl-leucinecyclosporin is used as the starting compound instead of cyclosporin A. The use of 4-(gamma-hydroxy)-N-methylleucinecyclosporin as the starting compound for such transformations is novel and part of the subject-matter of the present invention.

In general, the products which are obtained in these cases also predominantly have the configuration of a (D) amino acid.

The microbial hydroxylation of the gamma position of the amino acid in position D can be carried out using various microorganisms of the genus Actinomyces, for example using *Sebekia benihana* as described in Eur. J. Immunol. 1987, 17, 1359. The importance of this transformation is essentially that the immunosuppressive effect of cyclosporin is almost completely eliminated in one step.

While being of low toxicity, the compounds of the formula I possess advantageous biological properties, in particular that of exerting an inhibitory effect on human immunodeficiency virus (HIV), and can therefore be used as drugs in HIV infection. This inhibitory effect was observed to occur in suitable in-vitro experiments at a concentration of from 0.05 to 50 mg/l. The compounds of the formula I, and, where appropriate, their salts, can be used as drugs either alone or in suitable medicinal forms together with inorganic or organic pharmacologically indifferent auxiliary substances.

EXAMPLE 1

Preparation of 3-N-methyl-(D)-serine-4-(gamma-hydroxy)-N-methylleucinecyclosporin Eur. J. Immunol., 1987, Vol. 17, 1359, describes using *Sebekia benihana* to introduce a hydroxyl group into the gamma position of the N-methylleucine in position 4 of cyclosporin A by means of microbial transformation. This biotransformation can be used to prepare 3-N-methyl-(D)-serine-4-gamma-hydroxy-N-methylleucinecyclosporin from 3-N-methyl-(D)-serinecyclosporin. The strain which is used has the designation NRLL 11111 and belongs to the Actinoplanaceae family.

Starting Culture

Agar cultures of NRLL 11111 were grown at 27° for 10 days in a sterilized medium which was adjusted to pH 7 and consisted of 20 g of glucose, 10 g of yeast extract (Gistex), 10 g of peptone, 40 g of starch, 2 g of calcium carbonate, 40 g of agar and 1 l of water.

Preliminary Culture

The preliminary culture medium consisted of 35 g of glucose, 50 g of starch, 12.5 g of peptone, 50 g of malt extract, 22.5 g of yeast extract and 5 g of calcium carbonate in 5 l of water. In addition, this medium contained 5 ml of a solution of trace elements (1 ml of conc. sulfuric acid, 5 g of iron(II) sulfate heptahydrate, 50 mg of KI, 100 mg of boric acid, 4 g of zinc sulfate heptahydrate, 2 g of manganese(II) chloride tetrahydrate, 200 mg of copper sulfate pentahydrate and 2 g of cobalt chloride hexahydrate in 1 l of distilled water). Spores and mycelium of the starting culture were suspended in 10 ml of a 0.9% salt solution and the suspension was added to 100 ml of sterilized preliminary culture medium. This culture was shaken at 27° for 4 days on an orbital shaker at 200 revolutions/minute. After 4 days, the preliminary culture was diluted (1:10) with sterilized preliminary culture medium and shaken for a further 3 days.

Main Culture

The fermentation medium for the main culture (1 l of distilled water, 1 ml of the above-described solution of trace elements, 200 mg of ammonium molybdate, 255 mg of potassium hydrogen phosphate, 120 mg of potassium dihydrogen phosphate, 100 mg of magnesium sulfate heptahydrate, 50 mg of calcium chloride hexahydrate, 12.5 g of soya bean meal, 2.5 g of yeast extract, 10 g of starch, 10 g of dextrin and 10 g of cerelose) was adjusted to pH 7.3 and sterilized at 120° for 20 minutes. 10 ml of the preliminary culture obtained above ere then added and the mixture was shaken at 27° for 24 hours using an orbital shaker and, after 100 mg of 3-N-methyl-(D)-serinecyclo-sporin had been added, shaken for a further 3 days.

Isolation of 3-N-methyl-(D)-serine-4-(gamma-hydroxy)-N-methylleucinecyclosporin

The main culture is freed of mycelium by filtration and the filtrate is extracted 5× with dichloromethane. The combined extracts are concentrated in a rotary evaporator and the residue is chromatographed on 250 g of silica gel (Merck silica gel, particle size 0.4–0.063 mesh). Further chromatography of the cyclosporin fractions on 70 g of silica gel yields 15 mg of 3-N-methyl-(D)-serine-4-(gamma-hydroxy)-N-methylleucinecyclosporin as an amorphous powder. The optical rotation of this substance is $[alpha]_D = -166°$ (c=0.5, dichloromethane). This product can be crystallized from methanol, with the resulting crystals melting at 150–152°. In a $^1H$ NMR spectrum, in deuterated DMSO, the two methyl groups of the N-methyl-gamma-hydroxyleucine appear as singlets at 1.05 ppm.

EXAMPLE 2

Preparation of 3-N-methyl-(D)-serinecyclosporin

The preparation of this substance is described in the literature by D. Seebach et al., Helv. Chimica Acta, Vol. 76, 1564–1590, 1993.

This substance can be obtained in the following manner:

2a) 3-alpha-Methoxycarbonylcyclosporin 30 ml of a 1.6 molar solution of n-butyllithium in hexane are added dropwise, at 0° C. and under an inert gas atmosphere (argon), to a solution of 8.7 ml of diisopropylamine in 800 ml of dry THF. After 20 minutes at 0° C., the solution is cooled down to minus 78° C. and a solution, which has previously been cooled down to minus 78° C., of 10.0 g of cyclosporin A in 150 ml of dry tetrahydrofuran is added to it in portions. The resulting mixture is stirred at minus 78° C. for 1 hour, after which a stream of dry $CO_2$ gas is passed in. 6.4 ml of methyl chloroformate are then added dropwise and the mixture is stirred at minus 78° C. for 2 hours. After 1.1 ml of diisopropylamine have been added, the temperature is allowed to rise to 20° C. and the mixture is stirred at this temperature for 14 hours; it is then heated under reflux for 45 minutes. After the mixture has been cooled down to 20° C., 100 ml of 10% phosphoric acid are added and the aqueous phase is extracted with 600 ml of ethyl acetate. The aqueous phase is subsequently extracted several times with ethyl acetate. The organic extracts are combined, dried with magnesium sulfate and brought to dryness in vacuo. The resulting oil is chromatographed on 500 g of silica gel (0.02–0.05 mesh) using a 4:1 mixture of ethyl acetate and cyclohexane. Fractions which contain the product are combined and the solvent is removed in vacuo. 1.9 g of 3-alpha-methoxycarbonylcyclosporin are thus obtained as a colorless powder having a melting point of 138°.

2b) 3-N-Methyl-D-serinecyclosporin 2.4 ml of a 2.0 molar solution of lithium borohydride in THF are added dropwise, at 0° C., to a solution of 1.0 g of 3-alpha-methoxycarbonylcyclosporin in 30 ml of dry tetrahydrofuran. This mixture is stirred at 0° C. for 22 hours. 2 ml of distilled water are then added, followed by 10% hydrochloric acid, which is added dropwise, and a further 10 ml of distilled water. This mixture is shaken with 25 ml of ethyl acetate, after which the phases are separated and the aqueous phase is subsequently extracted a further 3× with 50 ml of ethyl acetate on each occasion. The combined extracts are dried with magnesium sulfate and concentrated to dryness in vacuo. The residue is chromatographed on 300 g of silica gel using ethyl acetate as the eluent. The product-containing fractions are combined and concentrated in vacuo, with 401 mg of 3-N-methyl-(D)-serinecyclosporin being obtained as a colorless amorphous powder. The melting point of this product is 128–130° C.

EXAMPLE 3

Preparation of 3-N-methyl-(D)-serine-4-(gamma-hydroxy)-N-methylleucinecyclosporin from 4-(gamma-hydroxy)-N-methylleucinecyclosporin 5 ml of a 1.6 molar solution of n-butyllithium in hexane are added dropwise, at 0° C. and under an inert gas atmosphere (argon), to a solution of 1.12 ml of diisopropylamine in 50 ml of dry THF. After 20 minutes at 0° C., the solution is cooled down to minus 78° C. and a solution, which has previously been cooled down to minus 78° C., of 1.2 g of 4-(gamma-hydroxy)-N-methylleucinecyclosporin in 50 ml of dry tetrahydrofuran is added to it in portions. The resulting mixture is stirred at minus 78° C. for 1 hour, after which monomeric formaldehyde is passed into the reaction mixture using a gentle stream of argon. The mixture is stirred at minus 78° C. for a further 2 hours. The temperature is then allowed to rise to 20° C., after which 10 ml of 10% phosphoric acid are added and the aqueous phase is extracted with 100 ml of ethyl acetate. The aqueous phase is subsequently extracted several times with ethyl acetate. The organic extracts are combined, dried with magnesium sulfate and brought to dryness in vacuo. The resulting oil is chromatographed on 100 g of silica gel (0.02–0.05 mesh) using ethyl acetate as the eluent. Fractions which contain the product are combined and the solvent is removed in vacuo. 5 mg of 3-N-methyl-(D)-serine-4-(gamma-hydroxy)-N-methylleucinecyclosporin are obtained in this way. According to all physicochemical criteria, the substance which is prepared in this manner is identical to the substance which is prepared as described in Example 1.

Test for Antiviral Activity

The T cell line MT4, which has been described by I. Myoshi et al. (Nature 294, pp. 770–771, 1981) was used for this test. HIV-1 (strain IIIB) was adsorbed on the cells for 2 hours at 37°. The inoculum was then removed and the infected cells were transferred to tissue culture plates which contained the test compound at different concentrations. In this context, the virus inoculum was chosen such that the concentration of viral p24 antigen increased exponentially in the cell supernatant up to the fourth day after the infection. On the third and fourth days after the infection, the cell supernatants were analyzed by ELISA for p24 antigen. $IC_{50}$ values were determined by comparing the p24 concentrations in the supernatant from the infected, substance-treated cells and in the supernatant from the untreated infected control cells. In this test, the $IC_{50}$ for 3-N-methyl-(D)-serine-4-gamma-hydroxy-N-methylleucinecyclosporin was found to be 0.1 mg/l. By comparison, the corresponding value for cyclosporin A is 0.5 mg/l.

I claim:

1. A cyclic peptide of the formula

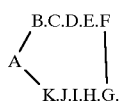   I in which A to K denote residues of the following amino acids:

A is a substituted homothreonine of the general formula

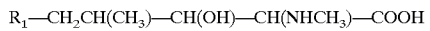   II in which $R_1$ is n-propyl or propenyl,

B is alpha-aminobutyric acid, valine, norvaline or threonine,

C is a (D)-amino acid of the formula

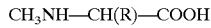   III in which
R is
  $C_2$–$C_6$ alkyl, alkenyl, alkynyl, straight-chain or branched, where these groups can additionally be substituted by hydroxyl, amino, $C_1$–$C_4$ alkylamino, $C_1$–$C_4$ dialkylamino, alkoxy or acyloxy,
  $COOR_2$, $CONHR_2$, where $R_2$ can be $C_1$–$C_4$ alkyl, straight-chain or branched,
  X—$R_3$, where X is O or S, and $R_3$ is $C_1$–$C_4$ alkyl, alkenyl or alkynyl, straight-chain or branched, and where, when X is S, $R_3$ can also be aryl or heteroaryl, halogen, cyano, or
  $CHR_4R_5$, where $R_4$ is hydrogen, methyl, ethyl or phenyl, and $R_5$ is hydrogen, hydroxyl or halogen, amino, $C_1$–$C_4$ alkylamino, $C_1$–$C_4$ dialkylamino, acyloxy, tert-butoxycarbonyl-aminoethoxy-ethoxy-acetyloxy, or alkoxycarbonyl, D is N-methyl-gamma-hydroxyleucine or N-methyl-gamma-acetyloxyleucine, E is valine, F, I and J are in each case N-methylleucine, G is alanine, H is (D)-alanine or (D)-serine, and K is N-methylvaline.

2. The cyclic peptide of the formula I as claimed in claim 1, in which the radical $R_1$ in A is propenyl, B is alpha-aminobutyric acid, D is N-methyl-gamma-hydroxyleucine, E is valine, F, I and J are in each case N-methylleucine, G is alanine, H is (D)-alanine and K is N-methylvaline.

3. The cyclic peptide of the formula I as claimed in claim 2, in which the radical R in the formula III is methyl, ethyl, propyl, allyl, propargyl, hydroxymethyl, hydroxyethyl, hydroxybenzyl, aminomethyl, methylaminomethyl, dimethylaminomethyl, ethylaminomethyl, diethylaminomethyl, propylaminomethyl, isopropylaminomethyl, dipropylaminomethyl, diisopropylaminomethyl, tert-butylaminomethyl, fluoromethyl, methoxymethyl, ethoxymethyl, methoxycarbonyl, ethoxycarbonyl, propoxycarbonyl, isobutyloxycarbonyl, methylaminocarbonyl, ethylaminocarbonyl, propylaminocarbonyl, isopropylaminocarbonyl, phenylaminocarbonyl, methoxycarbonylmethyl, ethoxycarbonylmethyl, propoxycarbonylmethyl, tert-butoxycarbonylmethyl, methoxy, ethoxy, propoxy, isopropoxy, n-butoxy, isobutoxy, tert-butoxy, hydroxyethoxy, methylthio, ethylthio, hydroxyethylthio, propylthio, isopropylthio, n-butylthio, isobutylthio, tert-butylthio, phenylthio, 2-pyridylthio or benzothiazol-2-ylthio.

4. 3-N-Methyl-(D)-serine-4-(gamma-hydroxy)-N-methylleucinecyclosporin.

5. A process for preparing compounds of the formula I as claimed in claim 1, in which C has the abovementioned meaning and D has the meaning of N-methyl-gamma-hydroxyleucine, which comprises hydroxylating a cyclic peptide of the formula I, in which D has the meaning of N-methylleucine, using a microorganism.

6. The process as claimed in claim 5, wherein the microorganism is *Sebekia benihana*.

7. A process for preparing compounds of the formula I, in which D has the meaning of N-methyl-gamma-hydroxyleucine, which comprises converting a cyclic peptide of the formula I, in which C is sarcosine and D is N-methyl-gamma-hydroxyleucine, into a polyanion using suitable bases and transforming this polyanion into the cyclic peptide as claimed in claim 1 by reacting it with suitable electrophiles.

8. A composition which comprises one or more cyclic peptides as claimed in claim 1 together with a pharmaceutically acceptable diluent or excipient.

9. A polyanion of the cyclic peptide of claim 1, wherein C is sarcosine and D is α-methyl-gamma hydroxyleucine.

10. A polyanion of 4-(gamma-hydroxy)-N-methylleucine-cyclosporin.

11. The cyclic peptide of claim 1, wherein $R_3$ is fluorine.

12. The cyclic peptide of claim 1, wherein $R_5$ is fluorine.

13. The cyclic peptide of claim 1, wherein the acyloxy of $R_5$ is acetyloxy.

14. The cyclic peptide of claim 1, wherein $R_5$ is butoxycarbonyl.

15. The cyclic peptide of claim 1, wherein the double bond of propenyl is trans-configured.

* * * * *